United States Patent [19]

Campbell et al.

[11] Patent Number: 4,572,909

[45] Date of Patent: Feb. 25, 1986

[54] 2-(SECONDARY AMINOALKOXYMETHYL) DIHYDROPYRIDINE DERIVATIVES AS ANTI-ISCHAEMIC AND ANTIHYPERTENSIVE AGENTS

[75] Inventors: Simon F. Campbell, Deal; Peter E. Cross, Canterbury; John K. Stubbs, Deal, all of England

[73] Assignee: Pfizer Inc., New York, N.Y.

[21] Appl. No.: 576,982

[22] Filed: Feb. 3, 1984

Related U.S. Application Data

[63] Continuation-in-part of Ser. No. 463,081, Feb. 2, 1983, abandoned.

[30] Foreign Application Priority Data

Mar. 11, 1982 [GB] United Kingdom ................ 8207180

[51] Int. Cl.[4] ................ C07D 211/90; A61K 31/455
[52] U.S. Cl. .................... 514/356; 546/321
[58] Field of Search ................ 544/333; 546/321, 283, 546/274, 280, 257, 271, 167, 284, 270; 424/251, 258, 266; 514/356

[56] References Cited

U.S. PATENT DOCUMENTS 4,430,333 2/1984 Campbell et al. ................ 546/321

FOREIGN PATENT DOCUMENTS 318101 7/1981 European Pat. Off. ............ 546/321

OTHER PUBLICATIONS

Schramm, M., "Novel Dihydropyridines with Positive Inotropic Action", Nature, vol. 303 (Jun. 9, 1983) pp. 535-537.

Bossert, F. et al, "4-Aryldihydropyridines", Angew. Chem. Int. Ed. Engl. 20, pp. 762-769 (1981).

Primary Examiner—Henry R. Jiles
Assistant Examiner—Dale A. Bjorkman
Attorney, Agent, or Firm—Charles J. Knuth; Albert E. Frost; James M. McManus

[57] ABSTRACT

A dihydropyridine compound of the formula

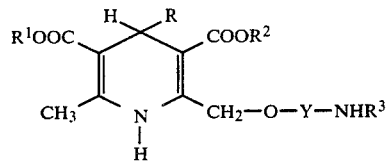

or a pharmaceutically acceptable acid addition salt thereof, wherein Y is $-(CH_2)_2-$, $-(CH_2)_3-$, $-CH_2CH(CH_3)-$ or $-CH_2C(CH_3)_2-$;

R is aryl or heteroaryl;

$R^1$ and $R^2$ are each independently $C_1-C_4$ alkyl or 2-methoxyethyl; and $R^3$ is hydrogen, $C_1-C_4$ alkyl, 2-($C_1-C_4$ alkoxy)ethyl, cyclopropylmethyl, benzyl, or $-(CH_2)_mCOR^4$ where m is 1, 2 or 3 and $R^4$ is hydroxy, $C_1-C_4$ alkoxy or $-NR^5R^6$ where $R^5$ and $R^6$ are each independently hydrogen or $C_1-C_4$ alkyl can be employed for treating or preventing a heart condition or hypertension.

17 Claims, No Drawings

2-(SECONDARY AMINOALKOXYMETHYL) DIHYDROPYRIDINE DERIVATIVES AS ANTI-ISCHAEMIC AND ANTIHYPERTENSIVE AGENTS

This is a continuation-in-part of U.S. patent application Ser. No. 463,081, filed Feb. 2, 1983, abandoned.

BACKGROUND OF THE INVENTION

This invention relates to certain dihydropyridines, specifically to certain 1,4-dihydropyridines having a substituted-amino containing group attached to the 2-position, which have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the invention, there are provided novel 1,4-dihydropyridine derivatives of the formula:

$$R^1OOC\diagup\diagdown COOR^2 \quad (I)$$
(1,4-dihydropyridine with H, R at 4-position; $CH_3$ and N-H in ring; $CH_2$—O—Y—$NHR^3$ at 2-position)

wherein
Y is —$(CH_2)_2$—, —$(CH_2)_3$—, —$CH_2CH(CH_3)$— or —$CH_2C(CH_3)_2$—;
R is aryl or heteroaryl;
$R^1$ and $R^2$ are each independently $C_1$–$C_4$ alkyl or 2-methoxyethyl; and
$R^3$ is hydrogen, $C_1$–$C_4$ alkyl, 2-($C_1$–$C_4$ alkoxy)ethyl, cyclopropylmethyl, benzyl, or —$(CH_2)_mCOR^4$ where m is 1, 2 or 3 and $R^4$ is hydroxy, $C_1$–$C_4$ alkoxy or —$NR^5R^6$ where $R^5$ and $R^6$ are each independently hydrogen or $C_1$–$C_4$ alkyl;
and their pharmaceutically acceptable acid addition salts.

DETAILED DESCRIPTION OF THE INVENTION

The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated d- and l- optically-active isomeric forms.

The pharmaceutically acceptable acid addition salts of the compounds of the formula (I) are those formed from acids which form non-toxic acid addition salts containing pharmaceutically acceptable anions, such as the hydrochloride, hydrobromide, sulphate, phosphate or acid phosphate, acetate, maleate, fumarate, lactate, tartrate, citrate and gluconate salts. The preferred salts are maleates.

The term "aryl" as used in this specification, includes, for example, phenyl optionally substituted by one or two substituents selected from nitro, halo, $C_1$–$C_4$ alkyl, $C_1$–$C_4$ alkoxy, hydroxy, trifluoromethyl, and cyano. It also includes 1- and 2-naphthyl.

The term "heteroaryl" as used in this specification includes, for example, benzofuranyl; benzothienyl; pyridyl optionally monosubstituted by methyl or cyano; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$–$C_4$ alkyl.

"Halo" means fluoro, chloro, bromo or iodo.

$C_3$ and $C_4$ alkyl and alkoxy groups can be straight or branched chain.

$R^3$ is preferably H, $CH_3$, benzyl, 2-methoxyethyl, —$CH_2COOCH_3$, —$CH_2COOC_2H_5$, —$CH_2CONH_2$, —$CH_2CONHCH_3$, or —$CH_2COOH$.

$R^3$ is most preferably H or $CH_3$.

R is preferably 2-chlorophenyl, 2-fluorophenyl, 2-methoxyphenyl, 3-chlorophenyl, 2-chloro-3-hydroxyphenyl, 2-chloro-6-fluorophenyl, unsubstituted phenyl or 2,3-dichlorophenyl.

$R^1$ is preferably $CH_3$.
$R^2$ is preferably $C_2H_5$.
Y is preferably —$(CH_2)_2$— or —$CH_2CH(CH_3)$—.
"m" is preferably 1.
Most preferably, R is 2-chlorophenyl.
Most preferably, Y is —$(CH_2)_2$—.

The most preferred compounds have the formula (I) wherein R is 2-chlorophenyl, $R^1$ is $CH_3$, $R^2$ is $C_2H_5$, $R^3$ is H or $CH_3$, and Y is —$(CH_2)_2$—.

The compounds of the formula (I) are primary or secondary amines and in one method they can be prepared by the removal of the amino-protecting group from the corresponding amino-protected dihydropyridines.

This general method can be illustrated in more detail as follows:

$$R^1OOC\diagup\diagdown COOR^2 \xrightarrow{\text{Removal of protecting group}} \text{Compound (I)}$$
(II) — dihydropyridine with $CH_3$, N–H, and $CH_2$—O—Y—$NR^3$(Q) substituent (Q=an amino-protecting group and R, $R^1$, $R^2$, $R^3$ and Y are as defined for formula [I]);

OR

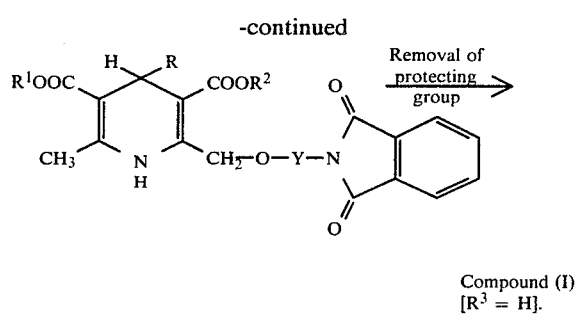

Compound (I)
[R³ = H].

[R, R¹, R² and Y are as defined for formula (I)].

One preferred amino-protecting group is benzyl. It is typically removed by hydrogenation, using e.g. $H_2/Pd$ on charcoal under acidic conditions in a suitable organic solvent, e.g. methanol. The acidic conditions are preferably obtained by using compound (II) in the form of an organic acid addition salt, e.g. as an oxalate or acetate salt.

A typical procedure involving the removal of a benzyl group is as follows. Compound (II) as an oxalate salt in methanol is added to a suspension of 10% prehydrogenated palladium on charcoal in methanol, and the mixture is then stirred under hydrogen at 50 p.s.i. for up to about 18 hours, e.g. overnight, and at room temperature. If necessary, heating at up to about 60° C. can be provided. The product can then be isolated and purified by conventional procedures.

When both Q and R³ are benzyl, hydrogenation under the above conditions normally only removes one of the benzyl groups. Further hydrogenation of the resulting monobenzyl product under the above conditions with fresh catalyst can then be used to remove the remaining benzyl group.

Many of the starting materials of the formula (II) in which Q is benzyl are described and claimed in our European patent application publication No. 0060674. Typical methods to the N-benzyl starting materials of the formula (II) are as follows:

(a) The benzyl-protected intermediates (II) can be prepared by the Hantzsch synthesis, as follows:

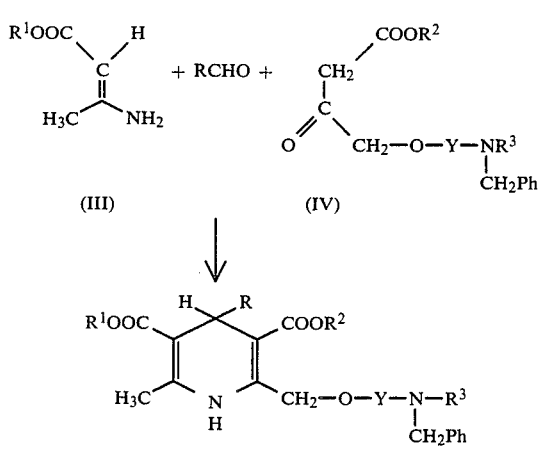

In a typical procedure, the ketoester (IV) and aldehyde are heated under reflux in a suitable organic solvent, e.g. a $C_1$–$C_4$ alkanol solvent such as ethanol, for about 15 minutes, and then the aminocrotonate (III) is added. Alternatively the aminocrotonate (III), ketoester (IV) and aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (II) can then be isolated and purified by conventional procedures.

The ketoesters (IV) are either known compounds or can be prepared by methods analogous to those of the prior art, such as the method illustrated in the Preparations hereinafter, which are essentially the method of Troostwijk and Kellogg, J.C.S. Chem. Comm., 1977, page 932. Similarly the amino-crotonates (III) are either known compounds or can be prepared by conventional procedures. Also the aldehydes are either known or can be prepared by known methods.

(b) The benzyl-containing intermediates (II) can also be prepared by the following process:

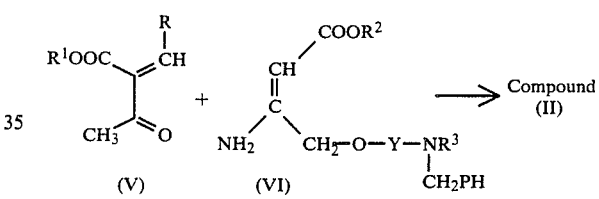

The crotonate (VI) is typically prepared in situ by reaction of the corresponding acetoacetate (IV):

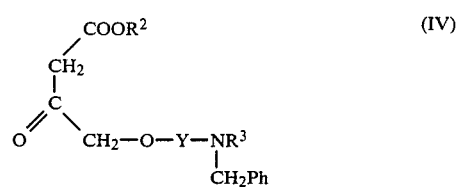

with ammonium acetate, e.g. by refluxing in a suitable organic solvent, e.g. a $C_1$–$C_4$ alkanol such as ethanol, for, say, up to an hour. The crotonate (VI) is then reacted with compound (V), typically by heating in the solvent for up to about 5 hours at 60° C.–130° C., e.g. under reflux. The product (II) can then be isolated and purified by conventional procedures.

The starting materials (V) are either known compounds or may be prepared by methods analogous to those of the prior art, see e.g. Can. J. Chem., 1967, 45, 1001.

The compounds of the formula (I) in which R³ is H can be prepared from the corresponding phthalimido derivatives according to conventional procedures, e.g.:

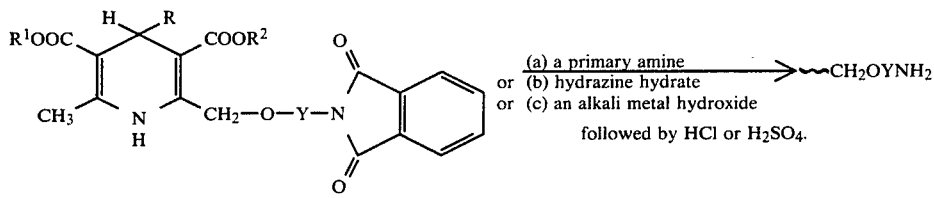

The prefered primary amine is methylamine. The preferred alkali metal hydroxide is potassium hydroxide.

The reaction using methylamine is typically carried out in ethanol at room temperature, with heating if necessary. The reaction using hydrazine hydrate is typically carried out in ethanol at the reflux temperature or below. The reaction using potassium hydroxide is typically carried out at room temperature (although with heating if necessary) in tetrahydrofuran, following by the addition of the acid and heating at the reflux temperature or below. In all cases the product can be isolated conventionally.

The phthalimido starting materials can again be obtained conventionally, e.g.:

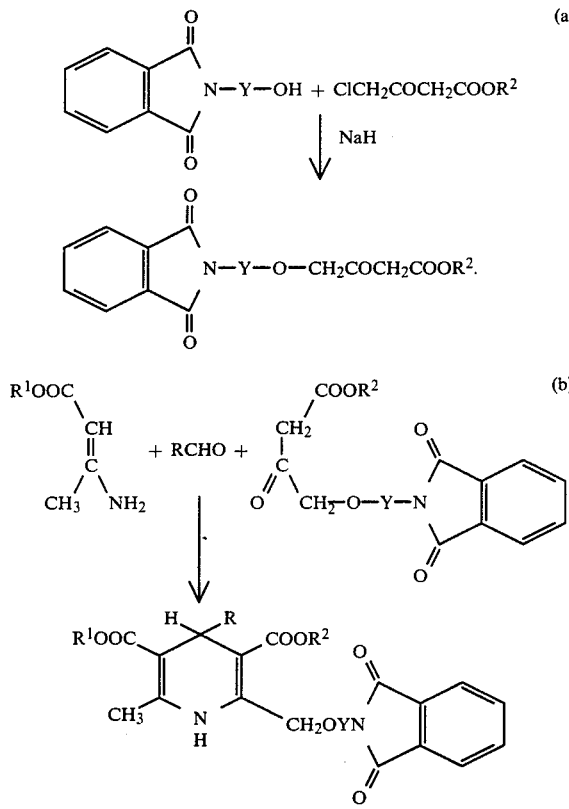

This is again the Hantzsch reaction.

Compounds of the formula (I) in which $R^3$ is H can also be purified to very high levels by reacting them with phthalic anhydride to form the phthalimido derivatives which can then be converted back to the compounds in which $R^3$ is H by the methods previously described.

To prepare compounds in which $R^3$ is $C_1$-$C_4$ alkyl, $-COOCH_2CCl_3$ can be used as the amino-protecting group. This can be removed in a conventional manner using zinc and either formic or acetic acid. The N-protected starting materials necessary for this process can be prepared as follows:

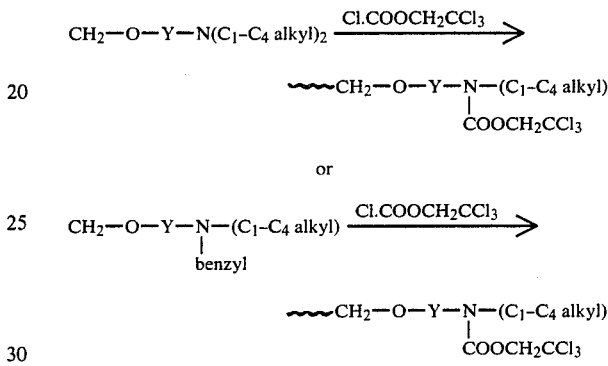

Typically the reaction with 2,2,2-trichloroethyl chloroformate is carried by heating the reactants at up to reflux temperature in e.g. toluene. Many of the dialkylamino and N-alkyl-N-benzylamino starting materials needed to prepared these N-protected intermediates are described and claimed in our corresponding European patent application publication No. 0060674, and others can be prepared analogously.

The compounds of the formula (I) where $R^3$=H can also be obtained from the corresponding azido compounds, the azido group being convertable to $-NH_2$ by reduction, e.g. with triphenylphosphine, or zinc and hydrochloric acid, or $H_2$/Pd, under conventional conditions.

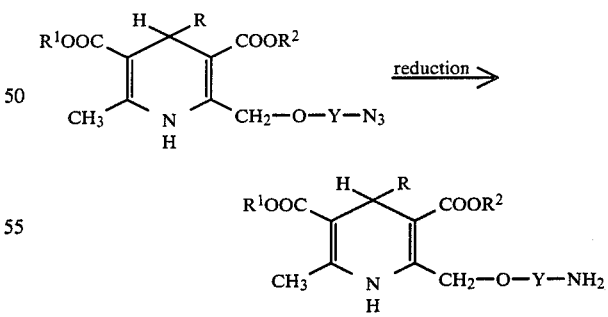

In a typical procedure using zinc dust, the reaction is carried out in methanol/aqueous hydrochloric acid. Heating is possible but is not generally necessary. Similarly hydrogenation can be carried out in e.g. methanol or ethanol in the presence of a catalyst such as Pd/CaCO$_3$ at room temperature.

Again the azido starting materials can be prepared by the Hantzsch synthesis under conditions similar to those previously described:

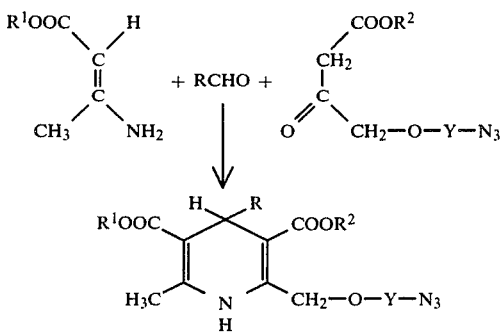

The azido-containing acetoacetates can also be obtained by conventional procedures:

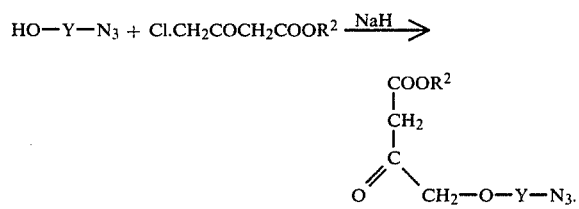

Similarly the azido starting materials can also be prepared analogously to route (b) above for preparing the N-benzyl starting materials.

Some of the compounds of the invention can be prepared from other compounds of the invention by conventional techniques, e.g.:

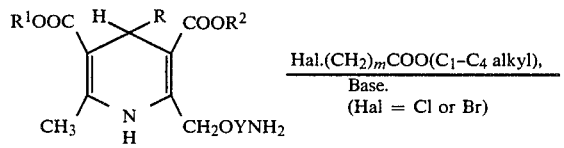

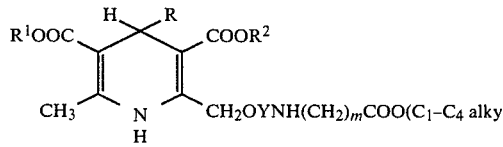

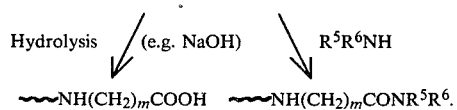

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will be in the range of from 2–50 mg daily for an average adult patient (70 kg). Thus for a typical adult patient, individual tablets or capsules are likely to contain from 1 to 10 mg of active compound, in a suitable pharmaceutically acceptable vehicle or carrier. Dosages for intravenous administration would be within the range 1 to 10 mg per single dose as required.

In a further aspect the invention provides a pharmaceutical composition comprising a compound of the formula (I), or a pharmaceutically acceptable acid addition salt thereof, together with a pharmaceutically acceptable diluent or carrier.

The invention also provides a compound of the formula (I), or a pharmaceutically acceptable acid addition salt thereof, for use in treating ischaemic heart disease, especially angina, or hypertension, in a human being.

The following Examples illustrate the invention: all temperatures are in °C.:

EXAMPLE 1

Preparation of 4-(2-chlorophenyl)-2-[2-(methylamino)ethoxymethyl]-3-ethoxycarbonyl-5-methoxycarbonyl-6-methyl-1,4-dihydropyridine, oxalate salt

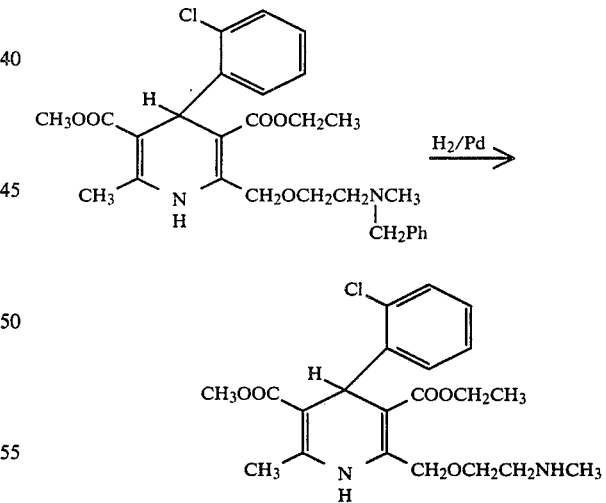

A solution of 2-[2-(N-benzyl-N-methylamino)ethoxymethyl]-4-[2-chlorophenyl]-3-ethoxycarbonyl-5-methoxycarbonyl-6-methyl-1,4-dihydropyridine, oxalate salt (4.3 g) in methanol (220 ml) was added to a suspension of 10% (by weight) palladium on charcoal (0.4 g) pre-hydrogenated in methanol (50 ml). Stirring under hydrogen at 50 p.s.i. and room temperature overnight resulted in complete removal of the benzyl group. After removal of the catalyst by filtration, the methanol was removed by evaporation and the residue crystallised from a little methanol to give the title compound (2.4 g), m.p. 211°.

Analysis %: Calculated for $C_{21}H_{27}ClN_2O_5.C_2H_2O_4$: C, 53.85; H, 5.70; N, 5.46; Found: C, 53.99; H, 5.76; N, 5.60.

The free base had a m.p. of 88°–90° (from ether).

ised in the form indicated, starting from the appropriate N-substituted dihydropyridine oxalate and $H_2$/Pd. It should be noted that hydrogenation of the N,N-dibenzyl starting material in Example 8 produced the monobenzyl product which was in turn used as the starting material in Example 9.

EXAMPLES 2-10

The following compounds were prepared similarly to the method described in Example 1 and were characterised in the form indicated.

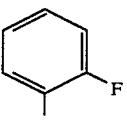

| Example No. | R | $R^3$ | Form Characterised | m.p. (°C.) | Analysis % (Theoretical in brackets) | | |
|---|---|---|---|---|---|---|---|
| | | | | | C | H | N |
| 2 | —Ph | —$CH_3$ | free base | 79–80 | 65.14 (64.93 | 7.33 7.26 | 7.09 7.21) |
| 3 | 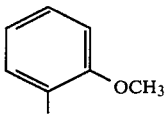 | —$CH_3$ | oxalate | 205–7 | 55.35 (55.64 | 5.84 5.84 | 5.60 5.64) |
| 4 | 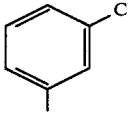 | —$CH_3$ | free base | 103–5 | 63.87 (63.14 | 7.60 7.23 | 6.56 6.70) |
| 5 | 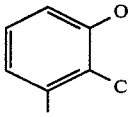 | —$CH_3$ | oxalate | 204–5 | 54.14 (53.85 | 5.71 5.70 | 5.57 5.46) |
| 6 | 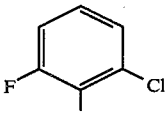 | —$CH_3$ | oxalate | 203–4 | 52.14 (52.22 | 5.68 5.49 | 5.29 5.30) |
| 7 | 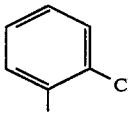 | —$CH_3$ | oxalate | 197–9 | 52.03 (52.03 | 5.41 5.30 | 5.06 5.30) |
| 8 | 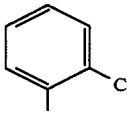 | —$CH_2Ph$ | oxalate | 185 | 59.18 (59.13 | 5.75 5.65 | 4.86 4.76) |
| 9 | 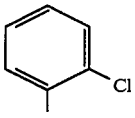 | —H | maleate | 169 | 54.83 (54.91 | 5.55 5.57 | 5.34 5.34) |
| 10 | 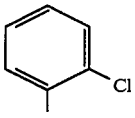 | —$CH_2CH_2OCH_3$ | oxalate | 105–7 | 53.57 (53.91 | 6.10 5.97 | 4.91 5.03) |

EXAMPLE 11

Preparation of 2-[(2-aminoethoxy)methyl]-4-(2-chlorophenyl)-3-ethoxycarbonyl-5-methoxycarbonyl-6-methyl-1,4-dihydropyridine maleate

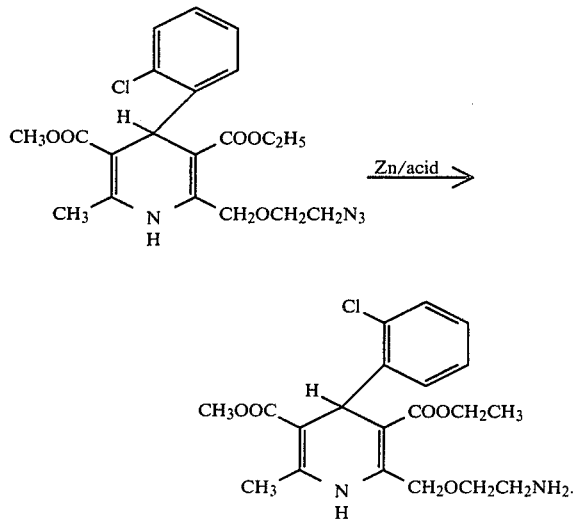

2-Azidoethanol (3 g) was converted to ethyl 4-(2-azidoethoxy)acetoacetate similarly to the method described in Preparation 3 hereinafter using ethyl 4-chloroacetoacetate, and the crude ketoester (not characterised) was used in the Hantzsch reaction using the method described in Preparation 9, i.e. by reacting it with methyl 3-aminocrotonate and 2-chlorobenzaldehyde. The crude Hantzsch product (not characterised) dissolved in methanol (250 ml) and 3N hydrochloric acid (200 ml) was stirred on a water bath at room temperature while zinc dust (15 g) was added portionwise over 10 minutes. After stirring a further 10 minutes the solution was decanted from excess zinc, the methanol evaporated and the aqueous acid residue washed with toluene (100 ml), basified with concentrated ammonia and extracted with methylene chloride (2×100 ml). The extracts were dried ($Na_2CO_3$), filtered and evaporated to dryness. The residue in toluene was chromatographed on a medium pressure column of silica (T.L.C. grade, Merck "Kieselgel" [Trade Mark] 60H, 7 g) eluting initially with toluene, changing gradually to methylene chloride and then to methylene chloride plus 3% methanol. Appropriate fractions were combined and converted to the maleate salt in ethyl acetate. Recrystallisation from acetone and ethyl acetate (1:1) gave the title compound (maleate salt) (190 mg, 1% yield from 2-azido ethanol) as a white solid, m.p. 169°, identical by t.l.c. with the product obtained in Example 9.

EXAMPLE 12

Preparation of 2-[2-aminoethoxy)methyl]-4-(2-chlorophenyl)-3-ethoxycarbonyl-5-methoxycarbonyl-6-methyl-1,4-dihydropyridine maleate

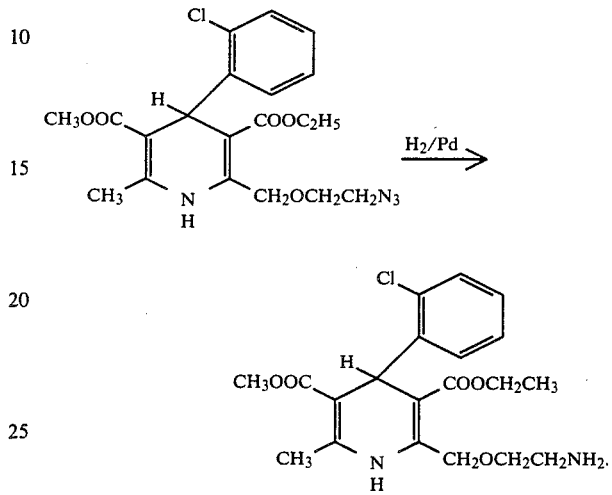

A suspension of 2-(2-azidoethoxy)methyl-4-(2-chlorophenyl)-3-ethoxycarbonyl-5-methoxycarbonyl-6-methyl-1,4-dihydropyridine (103 g) in ethanol (2.5 l) was stirred for 16 hours at room temperature under an atmosphere of hydrogen in the presence of 5% palladium on calcium carbonate (40 g). The reaction mixture was filtered and evaporated and the residue treated with a solution of maleic acid (22 g) in ethanol (100 ml). The reaction mixture was stirred at room temperature for two hours and then the resulting solid collected, washed with ethanol, and dried to give the title compound (100 g), m.p. 169°–170.5°.

Analysis %: Found: C,54.82; H,5.62; N,5.46 $C_{20}H_{25}ClN_2O_5 \cdot C_4H_4O_4$ requires: C,54.91; H,5.57; N,5.34.

EXAMPLES 13–15

The following compounds were prepared similarly to Example 12 from the appropriate azide and $H_2/Pd$:

| Example No. | R | Form characterised | m.p. (°C.) | Analysis % (Theoretical in brackets) C | H | N |
|---|---|---|---|---|---|---|
| 13 | ![2,6-dichlorophenyl] | ½ fumarate ½ hydrate | 171–173 | 51.7 (51.8 | 5.3 5.3 | 5.5 5.5) |
| 14 | ![phenyl] | fumarate ½ hydrate | 158–168 | 57.6 (57.7 | 6.2 6.3 | 5.8 5.6) |

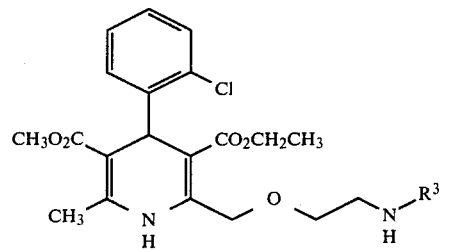

| Example No. | R | Form characterised | m.p. (°C.) | Analysis % (Theoretical in brackets) | | |
|---|---|---|---|---|---|---|
| | | | | C | H | N |
| 15 | ![F-phenyl] | fumarate | 152 | 56.95 (56.68 | 6.02 5.75 | 5.93 5.5) |

EXAMPLE 16

Methyl N-(2-{[4-(2,3-dichlorophenyl)-3-ethoxycarbonyl-5-methoxycarbonyl-6-methyl-1,4-dihydropyrid-2-yl]methoxy}ethyl)aminoacetate

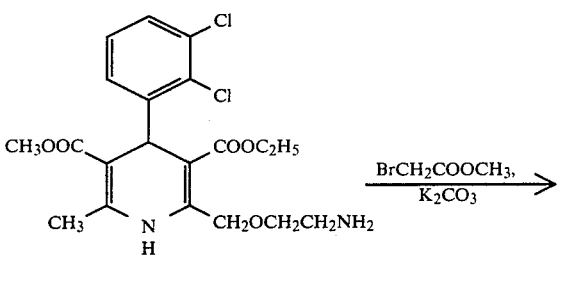

$\xrightarrow{\text{BrCH}_2\text{COOCH}_3, \text{K}_2\text{CO}_3}$

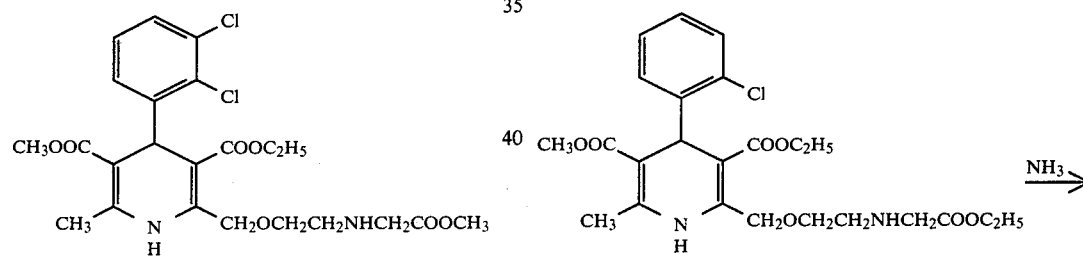

A solution of methyl bromoacetate (1.53 g) in acetonitrile (20 ml) was added dropwise over 30 minutes to a stirred, refluxing mixture of 2-[(2-aminoethoxy)methyl]-4-(2,3-dichlorophenyl)-3-ethoxycarbonyl-5-methoxycarbonyl-6-methyl-1,4-dihydropyridine (5.01 g) and potassium carbonate (2.76 g) in acetonitrile (60 ml). The mixture was then heated under reflux for 3 hours, filtered, and evaporated. The residue was partitioned between ethyl acetate and water and the organic layer washed with water, dried ($Na_2SO_4$), and evaporated. The residue was chromatographed on silica (t.l.c. grade Merck Kieselgel 60H, [Trade Mark] 40 g) eluting with dichloromethane plus 0–3% methanol. Appropriate fractions were combined and evaporated to give the title compound (2.10 g), m.p. 96°–98°.

Analysis %: Found: C,53.25; H,5.49; N,5.48; $C_{23}H_{28}Cl_2N_2O_7$ requires: C,53.60; H,5.48; N,5.44.

EXAMPLES 17 AND 18

The following compounds were prepared by the method described in Example 16 using appropriate starting materials.

| Example No. | $R^3$ | m.p. (°C.) | Analysis % or n.m.r. (Theoretical in brackets) | | |
|---|---|---|---|---|---|
| | | | C | H | N |
| 17 | —$CH_2CO_2CH_2CH_3$ | 78–80 | 58.26 (58.24 | 6.30 6.31 | 5.65 5.66) |
| 18 | —$CH_2CO_2CH_3$ | oil | n.m.r. (CDCl$_3$).τ values: 7.72 (1H, broad s); 6.96–7.51 (4H, m); 5.43 (1H, s); 4.78 (2H, s); 4.10 (2H, q); 3.78 (3H, s); 3.63 (3H, s); 3.3–3.7 (6H, m); 2.38 (3H, s); 1.20 (3H, t); | | |

EXAMPLE 19

2-(2-{[4-(2-Chlorophenyl)-3-ethoxycarbonyl-5-methoxycarbonyl-6-methyl-1,4-dihydropyrid-2-yl]methoxy}ethylamino)acetamide

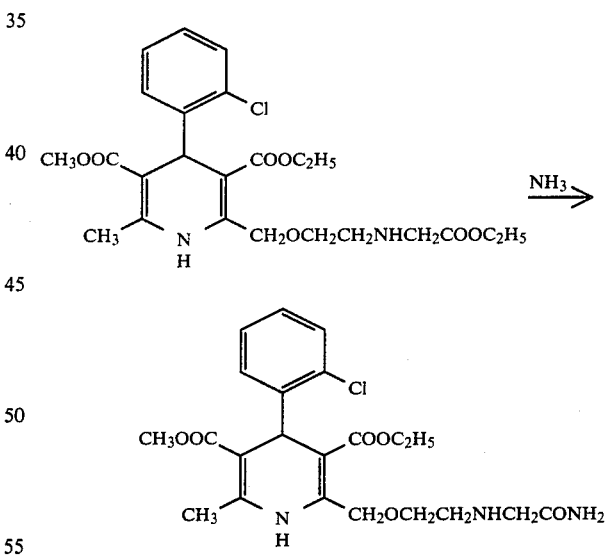

Ethyl N-(2-{[4-(2-chlorophenyl)-3-ethoxycarbonyl-5-methoxycarbonyl-6-methyl-1,4-dihydropyrid-2-yl]methoxy}ethyl)aminoacetate (2.50 g) in a mixture of ethanol (40 ml) and 0.880 aqueous ammonia (30 ml) was stirred at room temperature for four days and then evaporated. The residue was partitioned between ethyl acetate and water and the organic layer washed with water, dried (MgSO$_4$), and evaporated. The residue was chromatographed on silica (t.l.c. grade Merck Kieselgel 60H, [Trade Mark] 30 g) eluting with dichloromethane plus 0–5% methanol. Appropriate fractions were combined and evaporated. The residue was triturated with ethyl acetate and the resulting solid collected, washed with ethyl acetate, and dried to give the title compound (1.23 g), m.p. 126°–129°.

Analysis %: Found: C,56.78; H,6.06; N,8.68; $C_{22}H_{28}ClN_3O_6$ requires: C,56.71; H,6.06; N,9.02.

EXAMPLE 20

The following compound was prepared by the method described in Example 19 using the same dihydropyridine and methylamine.

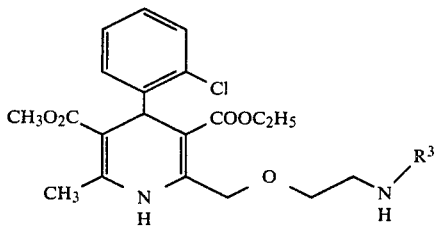

| Example No. | $R^3$ | m.p. (°C.) | Analysis % or n.m.r. (Theoretical in brackets) | | |
|---|---|---|---|---|---|
| | | | C | H | N |
| 20 | —CH$_2$CONHCH$_3$ | 123–124 | 57.80 (57.56 | 6.55 6.30 | 8.73 8.76) |

EXAMPLE 21

N-(2-{[4-(2-Chlorophenyl)-3-ethoxycarbonyl-5-methoxycarbonyl-6-methyl-1,4-dihydropyrid-2-yl]methoxy}ethyl)aminoacetic acid hemihydrate

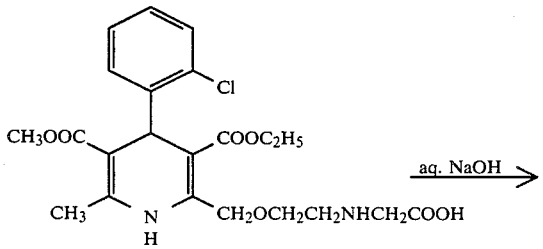

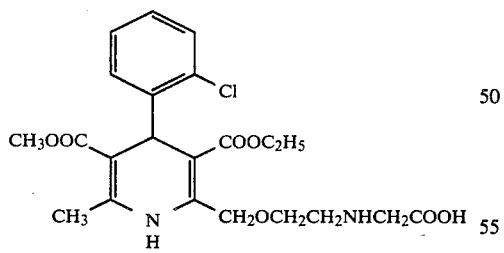

A solution of methyl N-(2-{[4-(2-chlorophenyl)-3-ethoxycarbonyl-5-methoxycarbonyl-6-methyl-1,4-dihydropyrid-2-yl]methoxy}ethyl)aminoacetate (2.40 g) in dioxane (80 ml) was treated with 1M aqueous sodium hydroxide solution (10 ml) and the mixture stirred at room temperature for 2 hours and then evaporated. The residue was purified by ion exchange chromatography (Bio-Rad AG 50W-X8, [Trade Mark], 200–400 mesh, cation form, 40 g) eluting with dioxane initially followed by 2% pyridine in water. Appropriate fractions were combined and evaporated to give the title compound as a hemihydrate (0.56 g), m.p. 140°–150° (decomp.).

Analysis %: Found: C,55.52; H,5.95; N,5.92; $C_{22}H_{27}ClN_2O_7.\frac{1}{2}H_2O$ requires: C, 55.52; H, 5.93; N, 5.89.

EXAMPLE 22

Preparation of 2-[(2-aminoethoxy)methyl]-4-(2-chlorophenyl)-3-ethoxycarbonyl-5-methoxycarbonyl-6-methyl-1,4-dihydropyridine maleate

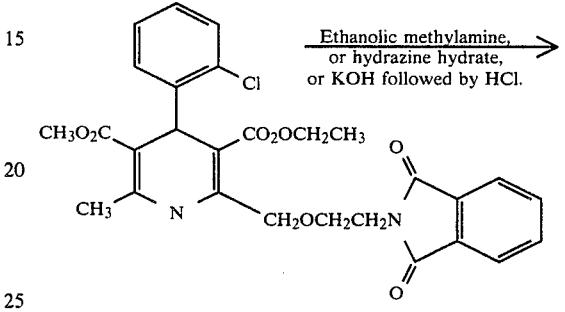

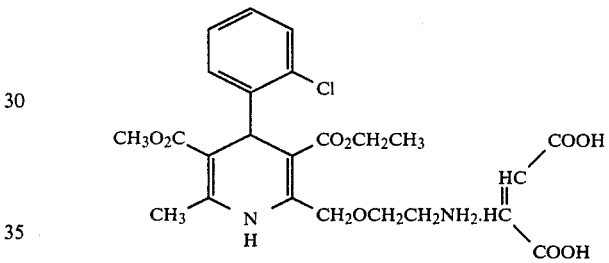

Method A (using ethanolic methylamine)

4-(2-Chlorophenyl)-3-ethoxycarbonyl-5-methoxycarbonyl-6-methyl-2-(2-phthalimidoethoxy)methyl-1,4-dihydropyridine (80 g) was stirred in 33% ethanolic methylamine solution (1067 ml) at room temperature for three hours. The solvent was then evaporated and the residue was slurried in industrial methylated spirits (300 ml) then filtered. To the filtrate was added maleic acid (17.4 g) and after stirring a precipitate was produced. This was collected by filtration and was washed with industrial methylated spirits. The solid was crystallized from industrial methylated spirits (430 ml) and dried at 55° to give the title compound (38.4 g) as a white solid confirmed spectroscopically to be identical with the products of Examples 9 and 12.

Method B (using hydrazine hydrate)

4-(2-Chlorophenyl)-3-ethoxycarbonyl-5-methoxycarbonyl-6-methyl-2-(2-phthalimidoethoxy)methyl-1,4-dihydropyridine (383 g) was stirred in refluxing ethanol containing hydrazine hydrate (106.7 g). After two hours, the reaction mixture was cooled and filtered. The filtrate was evaporated and the residue was dissolved in methylene chloride (2000 ml) and the solution was washed with water (2000 ml). The organic solution was evaporated and the residual oil was dissolved in industrial methylated spirit (1120 ml). To this solution was added maleic acid (82.5 g) and the resulting precipitate was collected, washed with industrial methylated spirit and dried at 55° to give the title compound (304 g) as a white solid, again confirmed spectroscopically to be the desired product.

Method C (using KOH followed by HCl).

4-(2-Chlorophenyl)-3-ethoxycarbonyl-5-methoxycarbonyl-6-methyl-2-(2-phthalimidoethoxy)methyl-1,4-dihydropyridine (15 g) was dissolved in a mixture of tetrahydrofuran (150 ml) and water (100 ml) containing potassium hydroxide (3.13 g). After stirring at room temperature for 1.5 hours 2N hydrochloric acid (100 ml) was added and the resulting slurry was refluxed for 2.5 hours. The solution was extracted twice with methylene chloride (2×100 ml) and the combined extracts were dried (MgSO4) and evaporated to leave an oil which was dissolved in industrial methylated spirits (57 ml). Maleic acid (3.24 g) was added and the resulting precipitate was collected, washed with industrial methylated spirits and dried at 55° to give the title compound (10.2 g) as an off-white solid, again confirmed spectroscopically to be the desired product.

-continued

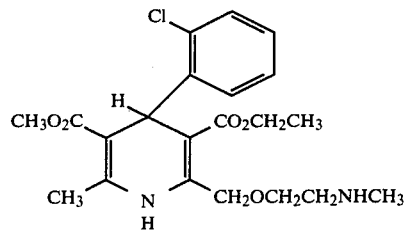

A mixture of 2-[2-(N-benzyl-N-methylamino)ethoxymethyl]-4-[2-chlorophenyl]-3-ethoxycarbonyl-5-methoxycarbonyl-6-methyl-1,4-dihydropyridine (4.8 g) and 2,2,2-trichloroethyl chloroformate (2.7 g) was heated in toluene at reflux for 20 hours. After cooling to room temperature, the mixture was stirred with 1N hydrochloric acid (50 ml) and extracted with ether. The extracts were evaporated to leave a crude oil (6.9 g) containing the corresponding 2-[2-(N-2,2,2-trichloroethoxycarbonyl-N-methylamino)ethoxymethyl]derivative.

EXAMPLES 22a-f

The following compounds were prepared similarly to the procedure of Example 22 Method A from the corresponding phthalimido derivative but using aqueous (40%) methylamine instead of ethanolic methylamine:

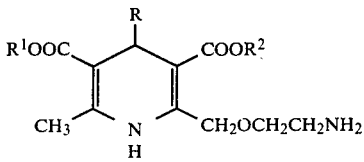

| Example | R | $R^1$ | $R^2$ | m.p. (°C.) | C | H | N |
|---------|---|-------|-------|------------|------|-----|------|
| (a) | 2,3-dichlorophenyl | $C_2H_5$ | $CH_3$ | 131–2° | 53.9 | 5.5 | 6.4 |
|     |                    |          |        |        | (54.2 | 5.5 | 6.3) |
| (b) | 2,3-dichlorophenyl * | $C_2H_5$ | $C_2H_5$ | 127–9° | 52.8 | 5.5 | 5.1 |
|     |                      |          |          |        | (52.7 | 5.6 | 5.3) |
| (c) | 2-chloro-3-trifluoromethylphenyl | $CH_3$ | $C_2H_5$ | 122° | 53.25 | 4.9 | 5.75 |
|     |                                   |        |          |       | (52.9 | 5.1 | 5.9) |
| (d) | 2,3-dichlorophenyl | $(CH_3)_2CH$ | $C_2H_5$ | 105–9° | 51.8 | 5.8 | 5.2 |
|     |                    |              |          |        | (51.8 | 6.0 | 5.1) |
| (e) | 2,3-dichlorophenyl | $CH_3OCH_2CH_2-$ | $C_2H_5$ | 88–90° | 54.5 | 5.8 | 6.0 |
|     |                    |                   |          |        | (54.2 | 5.8 | 5.75) |
| (f) | 2-chloro-pyrid-3-yl- | $CH_3$ | $C_2H_5$ | 129–131° | 55.6 | 5.9 | 10.6 |
|     |                      |        |          |          | (55.7 | 5.9 | 10.25) |

\* Isolated as the hemifumarate hemihydrate
  Isolated as the hemifumarate sesquihydrate

EXAMPLE 23

Preparation of 4-(2-Chlorophenyl)-2-[2-(N-methylamino)ethoxymethyl]-3-ethoxycarbonyl-5-methoxycarbonyl-6-methyl-1,4-dihydropyridine maleate

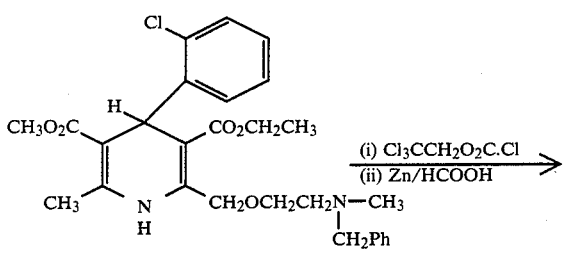

The said oil (3.0 g) was dissolved in dimethylformamide (10.5 ml) and formic acid (0.5 g) and at 5° zinc (0.7 g) was added.

The mixture was allowed to warm to room temperature and kept for three days at this temperature. The reaction mixture was then decanted and poured into water (100 ml) and acidified to pH1 with concentrated hydrochloric acid. The aqueous solution was washed with n-hexane (50 ml) then 0.88 ammonia solution was added to give a precipitate. This was collected and dried before dissolving in ethyl acetate. Maleic acid (0.34 g) was added followed by ether. After trituration, the solid was collected and dried to give a solid confirmed by NMR and IR to be (apart from the salt form) identical to the product of Example 1.

EXAMPLE 24

Preparation of 4-(2-chlorophenyl)-2-[2-(N-methylamino)ethoxymethyl]-3-ethoxycarbonyl-5-methoxycarbonyl-6-methyl-1,4-dihydropyridine maleate

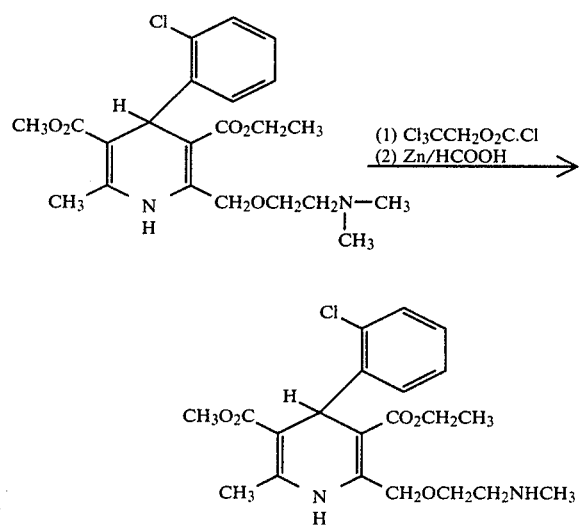

4-[2-chlorophenyl]-2-[2-(N,N-dimethylamino)ethoxymethyl]-3-ethoxycarbonyl-5-methoxycarbonyl-6-methyl-1,4-dihydropyridine (147.6 g) and 2,2,2-trichloroethylchloroformate (98.7 g) were stirred together in refluxing toluene for 20 hours. The reaction mixture was then cooled to room temperature and 1N hydrochloric acid (1147 ml) was added. The mixture was extracted twice with ether (2 × 1147 ml) and the extracts were bulked and evaporated to leave a crude oil (201.6 g) containing the corresponding 2-[2-(N-2,2,2-trichloroethoxycarbonyl-N-methylamino)ethoxymethyl]derivative.

This oil (196 g) was disssolved in dimethylformamide (686 ml) and formic acid (35.5 g) and the mixture was cooled to 5°. Zinc (50.5 g) was added in portions over 20 minutes and then the mixture was stirred at room temperature for 90 hours. The reaction mixture was decanted, added to water (1500 ml), and then taken to pH1 with concentrated hydrochloric acid. The aqueous solution was washed with n-hexane (500 ml) and the remaining aqueous phase was adjusted to pH10 with 0.88 ammonia solution. The resulting mixture was granulated and the solid was collected and dried to give the crude product (138 g). This solid was dissolved in hot ethyl acetate containing maleic acid (37.1 g) and on cooling the title compound was obtained (82.3 g) as a white solid confirmed spectroscopically to be identical to the product of Example 23.

EXAMPLE 25

Preparation of 2-(2-aminoprop-1-oxymethyl)-4-(2-chlorophenyl)-3-ethoxycarbonyl-5-methoxycarbonyl-6-methyl-1,4-dihydropyridine hemifumarate hemihydrate

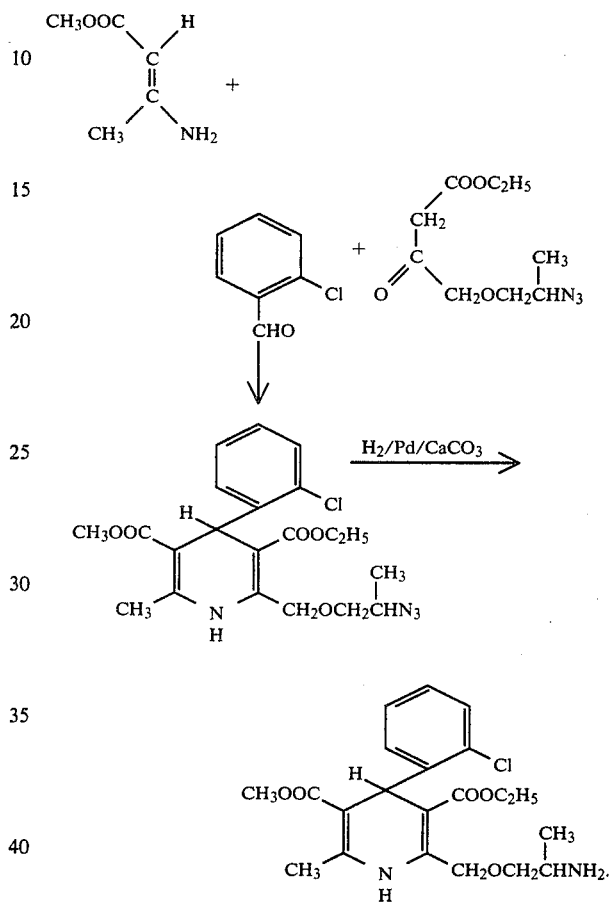

A mixture of ethyl 4-(2-azidoprop-1-oxy)acetoacetate (13.05 g), 2-chlorobenzaldehyde (8.3 g) and methyl 3-aminocrotonate (6.8 g) in methanol (80 ml) was heated under reflux for 19 hours, reduced to half-volume, and then cooled overnight at −20°. The resulting precipitate was collected, washed with a little cold methanol, and dried to give 2-(2-azidoprop-1-oxymethyl)-3-ethoxycarbonyl-5-methoxycarbonyl-6-methyl-1,4-dihydropyridine (4.0 g) as a pale yellow solid, m.p. 115°, characterised spectroscopically.

A suspension of the above product (4.0 g) in methanol (100 ml) was stirred under one atmosphere of hydrogen at room temperature in the presence of palladium on calcium carbonate (1.0 g) for 18 hours. The mixture was then filtered through "Solkafloc" (Trademark) and evaporated. The residue was dissolved in methanol (20 ml), treated with a warm solution of fumaric acid (1.00 g) in methanol (10 ml), and stored overnight at 0°. The resulting solid was collected, recrystallised from ethanol, and dried to give the title hemifumarate hemihydrate (2.4 g), m.p. 180°–183°

Analysis %: Found: C,56.46; H,6.63; N,5.68; Calculated for $C_{21}H_{27}ClN_2O_5 \cdot \frac{1}{2}C_4H_4O_4 \cdot \frac{1}{2}H_2O$: C,56.38; H,6.17; N,5.72.

The following Preparations illustrate the preparation of certain starting materials. All temperatures are in °C.:

PREPARATION 1

Preparation of Ethyl 4-[2-(N-benzyl-N-methylamino)ethoxy]acetoacetate

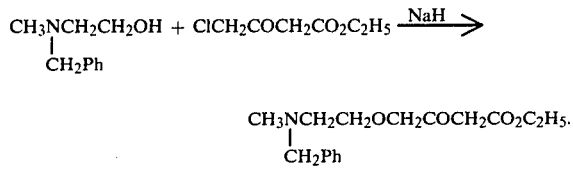

Sodium hydride (60% (by weight) in oil, 8 g) was stirred in dry tetrahydrofuran (THF) (100 ml) under nitrogen while 2-(N-benzyl-N-methylamino)ethanol (17 g) was added slowly. The warm mixture was stirred for 1 hour, then kept cool on a water bath at room temperature (20°) while a solution of ethyl 4-chloroacetoacetate (16.5 g) in dry THF (100 ml) was added dropwise over 3.5 hours. The mixture was stirred overnight at room temperature under nitrogen, then quenched with a little ethanol and poured onto ice (100 g) and concentrated hydrochloric acid (30 ml). The THF was removed by evaporation, and the residue washed with light petroleum (b.p. 60°–80°) to remove mineral oil. The residue was basified with solid sodium carbonate and extracted with ethyl acetate (200 ml and 100 ml). The combined extracts were dried ($Na_2CO_3$), filtered and evaporated to give the title compound as an oil (30 g), sufficiently pure for further use. N.m.r. spectrum in $CDCl_3$, δ values: 7.27 (5H,s); 4.12 (2H,q); 4.06 (2H,s); 3.45–3.70 (6H,m); 2.61 (2H,t); 2.25 (3H,s); 1.23 (3H,t).

The following acetoacetates were prepared similarly to the above, starting from the appropriate N-substituted 2-aminoethanol and ethyl 4-chloroacetoacetate, and were used directly without characterisation:

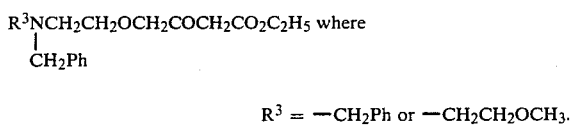

$R^3 = -CH_2Ph$ or $-CH_2CH_2OCH_3$.

PREPARATION 2

Preparation of 2-[2-(N-benzyl-N-methylamino)ethoxymethyl]-4-(2-chloro-phenyl)-3-ethoxycarbonyl-5-methoxycarbonyl-6-methyl-1,4-dihydropyridine, oxalate salt

Method (a)

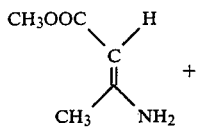

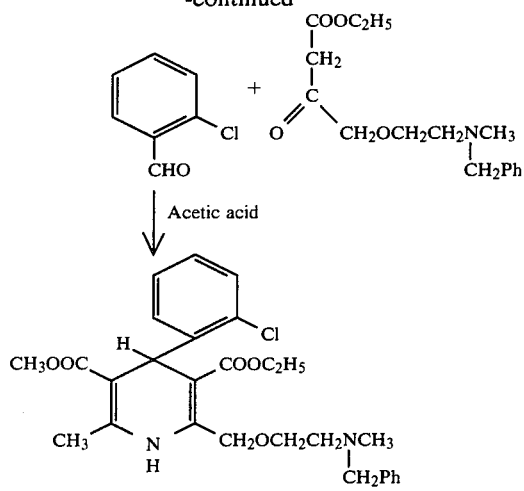

Ethyl 4-[2-(N-benzyl-N-methylamino)ethoxy]acetoacetate (25 g), 2-chlorobenzaldehyde (11 g), methyl 3-aminocrotonate (9.1 g) and acetic acid (5 ml) in ethanol (100 ml) were mixed and heated under reflux for 3.5 hours. The cooled reaction mixture was then evaporated to dryness and the residue partitioned between 2N hydrochloric acid (200 ml) and methylene chloride (300 ml). The methylene chloride solution was washed with saturated sodium carbonate solution (200 ml), dried ($MgSO_4$), filtered and evaporated to dryness. The residue in ether was treated with an excess of oxalic acid dissolved in ether to precipitate the crude product. The precipitate was recrystallized from methanol to give the title compound (6.5 g) as a white solid, m.p. 181°.

Analysis Calculated for $C_{28}H_{33}ClN_2O_5.C_2H_2O_4$: C, 59.75; H, 5.85; N, 4.65 Found: C, 59.42; H, 5.85; N, 4.39.

Method (b)

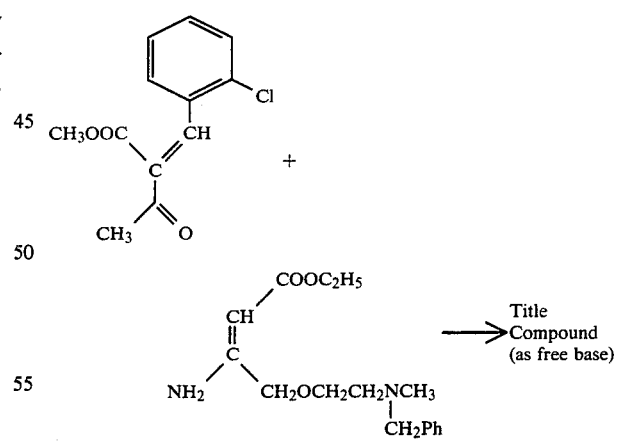

Ethyl 4-[2-(N-benzyl-N-methylamino)ethoxy]acetoacetate (141 g) and ammonium acetate (37.3 g) in ethanol (280 ml) were heated gently under reflux for 20 minutes. The methyl 2-(2-chlorobenzylidine)acetoacetate (115 g) was added and heating under reflux continued for 4 hours. The cooled reaction mixture was evaporated to dryness, re-dissolved in toluene (200 ml), and extracted with 2N hydrochloric acid (2×150 ml). The thick oily layer in the aqueous phase, and the aqueous phase itself, were extracted with methylene chloride (400 ml and 200 ml), and the combined extracts were washed with excess saturated sodium carbonate solution and dried ($Na_2CO_3$). The methylene chloride was removed by evaporation and the residue in toluene plus 20% petrol was filtered through a medium pressure column of silica (T.L.C. grade, Merck "Kieselgel" [Trade Mark] 60H, 100 g) eluting with toluene plus 20% petrol (500 ml) and then toluene (1 liter). The combined eluates were evaporated to dryness to give the crude title compound as the free base, an oil (177 g), sufficiently pure by t.l.c. for use in the subsequent hydrogenation step.

The following starting materials were also prepared similarly to (b) above, starting from the appropriate N-substituted acetoacetates and ammonium acetate, and were used directly without characterisation:

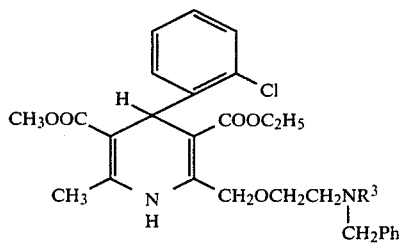

where $R^3$ = —$CH_2Ph$ or —$CH_2CH_2OCH_3$.

PREPARATION 3

2-(2-Azidoethoxy)methyl-4-(2-chlorophenyl)-3-ethoxycarbonyl-5-methoxycarbonyl-6-methyl-1,4-dihydropyridine

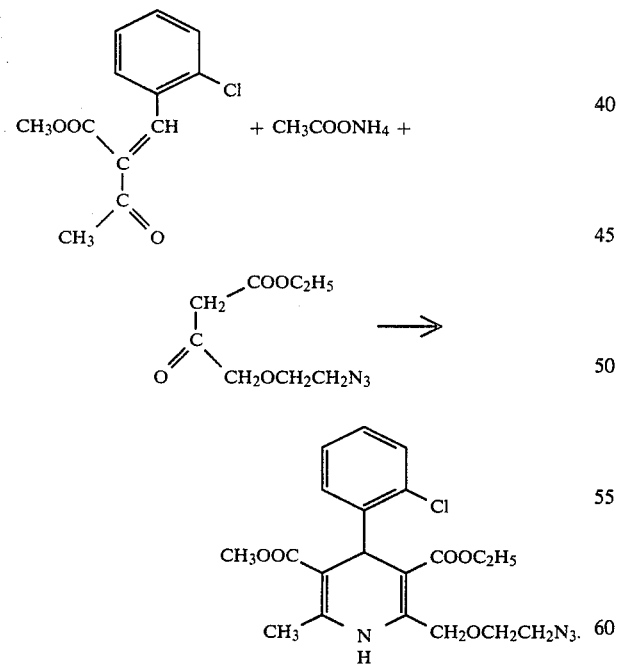

A solution of 2-azidoethanol (160 g) in tetrahydrofuran (300 ml) was added over 40 minutes to a suspension of sodium hydride (114 g; 80% dispersion in oil) in tetrahydrofuran (500 ml). The mixture was stirred at room temperature for 1 hour, then cooled in ice water and treated dropwise with a solution of ethyl 4-chloroacetoacetate (276 g) in tetrahydrofuran (250 ml) over 2 hours. The mixture was stirred at room temperature for 16 hours, diluted with ethanol (150 ml), and the pH adjusted to 6–7 with 4M hydrochloric acid. Sufficient water was added to dissolve the solid present and the layers were separated. The organic layer was evaporated and the residue diluted with water (600 ml) and evaporated. The residue was partitioned between ethyl acetate and water and the aqueous layer extracted twice with ethyl acetate. The combined ethyl acetate extracts were dried ($MgSO_4$) and evaporated to give ethyl 4-(2-azidoethoxy)acetoacetate as a brown oil, which was shown by g.l.c. to be 73% pure. A mixture of this crude product and ammonium acetate (92.3 g) in ethanol (600 ml) was heated under reflux for 1 hour, allowed to cool to room temperature, and treated with methyl 2-(2-chlorobenzylidene)-acetoacetate (286.6 g). The mixture was heated under reflux for 5.5 hours and then evaporated. The residue was stirred with methanol (1.5 l) for 16 hours and the resulting solid collected, washed twice with methanol, dried, and recrystallised from methanol to give the title compound (78 g), m.p. 145°–146°.

Analysis %: Found: C, 55.39; H, 5.37; N, 13.01 Calculated for $C_{20}H_{23}ClN_4O_5$: C, 55.23; H, 5.33; N, 12.88.

PREPARATIONS 4 TO 6

The following azides were prepared similarly to Preparation 3 from appropriate starting materials:

| Preparation No. | R | m.p. (°C.) | Analysis % (Theoretical in brackets) | | |
|---|---|---|---|---|---|
| | | | C | H | N |
| 4 | 2,3-dichlorophenyl | 141 | 50.88 (51.18 | 4.78 4.73 | 11.73 11.94) |
| 5 | phenyl | 124 | 59.64 (59.99 | 6.11 6.04 | 13.98 13.99) |
| 6 | 2-fluorophenyl | 129–130 | n.m.r. in $CDCl_3$: δ = 7.14 (5H,m); 5.28(1H,s); 4.80(2H,s); 4.04(2H,q); 3.65(4H,m); 3.62(3H,s); 2.35(3H,s); 1.20(3H,t). | | |

PREPARATION 7

Preparation of ethyl 4-[2-(phthalimido)ethoxy]acetoacetate

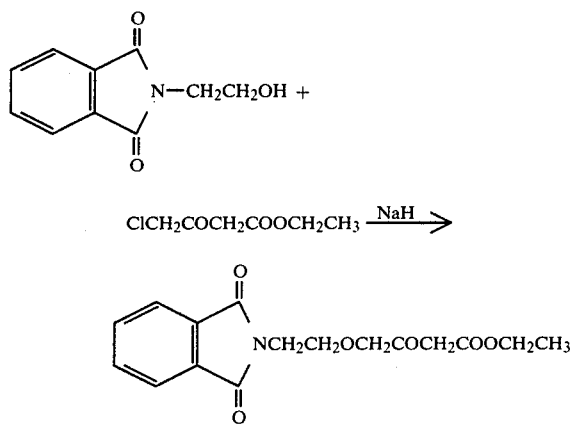

Sodium hydride (57% [by weight] in oil, 66.1 g) was stirred in dry tetrahydrofuran (500 ml) under nitrogen at −10° while N-(2-hydroxyethyl)phthalimide (150 g) was added. To this slurry was added at −10° a solution of ethyl 4-chloroacetoacetate (129.3 g), in dry tetrahydrofuran, over 1 hour. The reaction mixture was then allowed to warm to room temperature and stirring was continued for 18 hours. This mixture was poured into 1N hydrochloric acid (800 ml) and ethyl acetate was added (750 ml). The aqueous layer was washed with ethyl acetate (300 ml) and the organic solutions were combined. After washing with water (300 ml), the ethyl acetate was evaporated to give the title compound as a crude oil (243 g), sufficiently pure for further use.

N.m.r. spectrum in CDCl₃, δ values: 7.80 (4H, m); 4.15 (2H, s); 4.10 (2H, q); 3.92 (2H, t); 3.78 (2H, t); 3.49 (2H, s); 1.22 (3H, t).

PREPARATION 8

Preparation of 4-(2-Chlorophenyl)-3-ethoxycarbonyl-5-methoxycarbonyl-6-methyl-2-(2-phthalimidoethoxy)methyl-1,4-dihydropyridine (A.) From 2-[(2-aminoethoxy)methyl]-4-(2-chlorophenyl)-3-ethoxycarbonyl-5-methoxycarbonyl-6-methyl-1,4-dihydropyridine

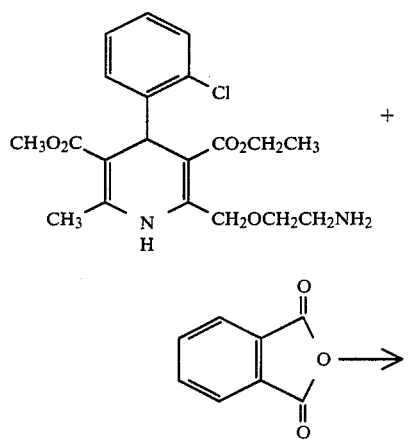

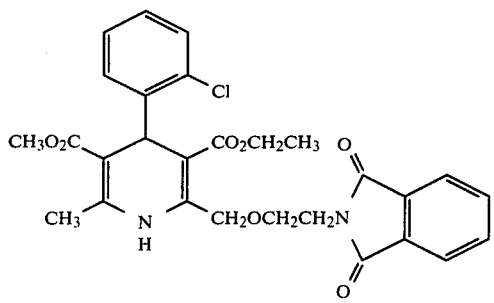

2-[2-Aminoethoxy)methyl]-4-(2-chlorophenyl)-3-ethoxycarbonyl-5-methoxycarbonyl-6-methyl-1,4-dihydropyridine (2.0 g) and phthalic anhydride (0.73 g) were stirred in refluxing acetic acid (20 ml) for 2.5 hours. After cooling, the insoluble material was collected and stirred in methanol (10 ml). Filtration gave the title compound (1.0 g) as a white solid, m.p. 146°–147°.

Analysis %: Found: C, 62.18; H, 5.02; N, 5.20 Calculated for C₂₈H₂₇ClN₂O₇: C, 62.39; H, 5.05; N, 5.20.

(B.) From ethyl 4-[2-(phthalimido)ethoxy]acetoacetate

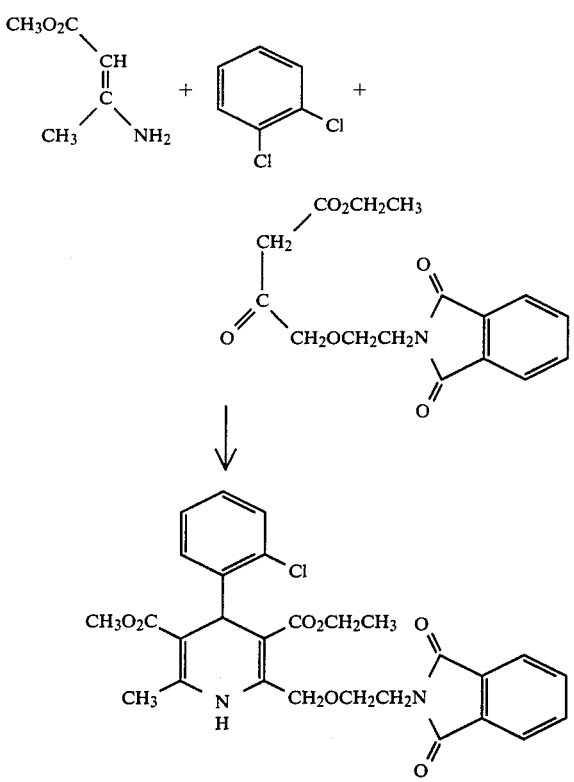

Ethyl 4-[2-(phthalimido)ethoxy]acetoacetate (200 g) was dissolved in isopropanol (1000 ml) and to this was added 2-chlorobenzaldehyde (88.1 g) and methyl 3-aminocrotonate (72.2 g). The mixture was refluxed for 21 hours then the methanol was evaporated to leave an oil which was dissolved in acetic acid (1000 ml). After granulating overnight, the precipitate was collected, washed with acetic acid then slurried in methanol (300 ml). Filtration gave the title compound the n.m.r. and ir of which were identical with those of the material prepared by part (A) above.

The following phthalimide intermediates were prepared similarly to Preparation 8(B) from appropriate starting materials.

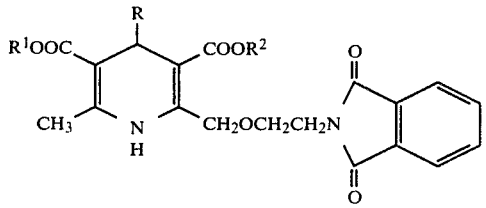

| Preparation | R | R¹ | R² | m.p. (°C.) | Analysis % (Theoretical in brackets) | | |
|---|---|---|---|---|---|---|---|
| | | | | | C | H | N |
| (a) | 2,3-dichlorophenyl | $C_2H_5$ | $CH_3$ | 165° | 58.5 (58.65 | 4.7 4.6 | 5.0 4.9) |
| (b) | 2,3-dichlorophenyl | $C_2H_5$ | $C_2H_5$ | 149–150° | 59.45 (59.3 | 4.9 4.8 | 4.8 4.8) |
| (c) | 2-chloro-3-trifluoro-methyl-phenyl | $CH_3$ | $C_2H_5$ | 179° | 57.2 (57.4 | 4.45 4.3 | 4.8 4.6) |
| (d) | 2,3-dichlorophenyl | $(CH_3)_2CH$ | $C_2H_5$ | 174–180° | — | | |
| (e) | 2,3-dichlorophenyl | $CH_3OCH_2CH_2$ | $C_2H_5$ | 106–9° | 56.7 (56.7 | 4.8 5.1 | 4.5 4.4) |
| (f) | 2-chloropyrid-3-yl | $CH_3$ | $C_2H_5$ | 123–5° | 60.05 (60.1 | 4.9 4.85 | 7.6 7.8) |

PREPARATION 9

Preparation of 2-(2-Azidoethoxy)methyl-4-(2-chlorophenyl)-3-ethoxycarbonyl-5-methoxycarbonyl-6-methyl-1,4-dihydropyridine

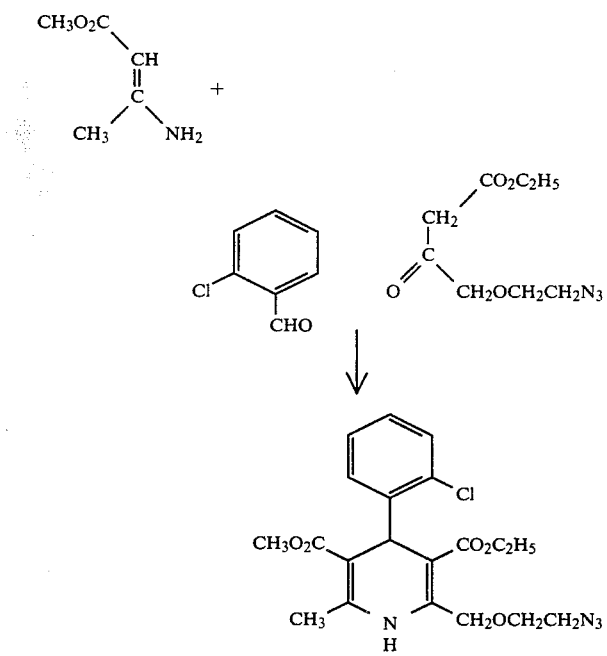

Ethyl 4-(2-azidoethoxy)acetoacetate (46.4 g), prepared from 2-azidoethanol similarly to the method described in Preparation 3, was reacted with methyl 3-aminocrotonate (24.8 g) and 2-chlorobenzaldehyde (30.3 g) in methanol (150 ml) at reflux for 18 hours. After cooling to room temperature, the resulting solid was collected, washed twice with methanol and dried to give the title compound (28 g). The product could be crystallised from methanol, acetone or ethyl acetate. It was used directly.

PREPARATION 10

Preparation of ethyl 4-(2-azidoprop-1-oxy)acetoacetate

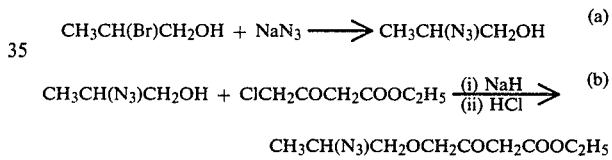

A mixture of 2-bromopropan-1-ol (J. Am. Chem. Soc., 7681, 96, [1974]) (19.75 g) and sodium azide (10.0 g) was heated on a steam-bath for four days, allowed to cool to room temperature, and then washed four times with ether. The combined ether washings were filtered and evaporated to give 2-azidopropan-1-ol (12.3 g) as a pale brown oil which was shown by g.l.c. to be 98% pure.

A solution of the 2-azidopropan-1-ol (10.1 g) in tetrahydrofuran (100 ml) was added over two minutes to a stirred, ice-cooled suspension of sodium hydride (6.6 g; 80% dispersion in oil) in tetrahydrofuran (50 ml). The mixture was stirred for 15 minutes with ice-cooling and then treated over 20 minutes with a solution of ethyl 4-chloroacetoacetate (16.4 g) in tetrahydrofuran (150 ml). The mixture was stirred at room temperature for 16 hours and evaporated. The residue was diluted with water, washed twice with ether, acidified with 2M hydrochloric acid, and extracted three times into ether. The combined ether extracts were dried ($Na_2SO_4$) and evaporated to give crude ethyl 4-(2-azidoprop-1-oxy)acetoacetate (20 g), used directly.

PREPARATION 11

Preparation of 2-chloro-3-trifluoromethylbenzaldehyde

2-Chloro-1-trifluoromethylbenzene (54.15 g) was dissolved in dry tetrahydrofuran (500 ml) and stirred while cooling to −68° under a stream of dry nitrogen. (The whole reaction is carried out under dry nitrogen until the addition of distilled water.) To this was added n-butyl lithium (180 ml of a 1.6M solution in hexane) dropwise keeping the temperature below −60°. After stirring at −68° for a further 2 hours, a solution of dimethylformamide (22 ml) in dry tetrahydrofuran (100 ml) was added dropwise keeping the temperature below −60°. The reaction mixture was allowed to warm to room temperature slowly over 17 hours and distilled water (200 ml) was then added. The organic phase was separated off and the aqueous liquors were extracted with ether (100 ml). The combined ether extracts plus the organic phase were washed with saturated brine, dried (MgSO$_4$), filtered and evaporated to give 61.5 g of an orange oil, being the crude title compound.

This oil was then added to an aqueous sodium bisulphite solution (65 g in 600 ml distilled water) and heated at 60° for 0.5 hours. The solution was extracted with methylene chloride (3×100 ml) and, after acidification of the aqueous phase with concentrated sulphuric acid to pH1, was heated at 100° for a further 0.5 hours. The resultant aqueous solution was extracted with methylene chloride (3×200 ml) and the combined organic extracts were dried (MgSO$_4$), filtered and evaporated to give 42 g of a colourless solid which was crystallised from hexane to give the title compound, m.p. 43°–44°.

Analysis %: Found: C, 45.9; H, 2.0 Calculated for C$_8$H$_4$F$_3$ClO: C, 46.1; H, 2.0.

PREPARATION 12

Preparation of 2,3-dichlorobenzaldehyde

A similar route to that described in the previous Preparation, starting from 1,2-dichlorobenzene, proved to be a superior method for preparing the title compound, m.p. 62°.

Analysis %: Found: C, 47.62; H, 2.38 Calculated for C$_7$H$_4$Cl$_2$O: C, 48.04; H, 2.30.

Activity Data

The molar concentration of the compounds required to reduce the response by 50% in the test specified on pages 8–9 is given below (IC$_{50}$ values) (1M=1 gm.mole/liter). The smaller the concentration the more active the compound, i.e., the most active compounds are the products of Examples 1, 9, 11, 12, 22, 23 and 24.

| IC$_{50}$ Values | |
|---|---|
| Compound | IC$_{50}$ |
| Product of Example 1 | $3.2 \times 10^{-9}$ M |
| Product of Example 2 | $3.2 \times 10^{-8}$ M |
| Product of Example 3 | $2 \times 10^{-8}$ M |
| Product of Example 4 | $6.3 \times 10^{-8}$ M |
| Product of Example 5 | $4 \times 10^{-8}$ M |
| Product of Example 6 | $2 \times 10^{-7}$ M |
| Product of Example 7 | $1.3 \times 10^{-8}$ M |
| Product of Example 8 | $5 \times 10^{-8}$ M |
| Product of Example 9 | $3.2 \times 10^{-9}$ M |
| Product of Example 10 | $2.5 \times 10^{-8}$ M |
| Product of Example 11 | $3.2 \times 10^{-9}$ M |
| Product of Example 12 | $3.2 \times 10^{-9}$ M |
| Product of Example 13 | $6.3 \times 10^{-9}$ M |
| Product of Example 14 | $1.6 \times 10^{-7}$ M |
| Product of Example 15 | $1.8 \times 10^{-8}$ M |
| Product of Example 19 | $4 \times 10^{-9}$ M |
| Product of Example 20 | $2.2 \times 10^{-8}$ M |
| Product of Example 22 | $3.2 \times 10^{-9}$ M |
| Product of Example 23 | $3.2 \times 10^{-9}$ M |
| Product of Example 24 | $3.2 \times 10^{-9}$ M |

We claim:

1. A dihydropyridine compound of the formula $$R^1O_2C\underset{CH_3}{\overset{H\quad R}{\diagdown}}\underset{N}{\diagdown}\underset{H}{\overset{CO_2R^2}{\diagup}}CH_2-O-Y-NHR^3$$

or a pharmaceutically acceptable acid addition salt thereof, wherein

Y is —(CH$_2$)$_2$—, —(CH$_2$)$_3$—, —CH$_2$CH(CH$_3$)— or —CH$_2$C(CH$_3$)$_2$—;

R is aryl; R$^1$ and R$^2$ are each independently C$_1$–C$_4$ alkyl or 2-methoxyethyl; and R$^3$ is hydrogen, C$_1$–C$_4$ alkyl, 2-(C$_1$–C$_4$ alkoxy)ethyl, cyclopropylmethyl, benzyl, or —(CH$_2$)$_m$COR$^4$ where m is 1, 2 or 3 and R$^4$ is hydroxy, C$_1$–C$_4$ alkoxy or —NR$^5$R$^6$ where R$^5$ and R$^6$ are each independently hydrogen or C$_1$–C$_4$ alkyl; wherein aryl is phenyl; phenyl substituted by one or two of nitro, halo, C$_1$–C$_4$ alkyl, C$_1$–C$_4$ alkoxy, hydroxy, trifluoromethyl or cyano; 1-naphthyl; or 2-naphthyl.

2. A compound according to claim 1 wherein the aryl is 2-chlorophenyl or 2,3-dichlorophenyl.

3. A compound according to claim 1 wherein R$^3$ is H, CH$_3$ or —(CH$_2$)$_m$COR$^4$ wherein m is 1.

4. A compound according to claim 1 wherein R$^1$ is CH$_3$.

5. A compound according to claim 1 wherein R$^2$ is C$_2$H$_5$.

6. A compound according to claim 1 wherein Y is —(CH$_2$)$_2$—.

7. A compound according to claim 1 wherein R is 2-chlorophenyl or 2,3-dichlorophenyl, R$^1$ is CH$_3$, R$^2$ is C$_2$H$_5$, Y is —(CH$_2$)$_2$— and R$^3$ is H or CH$_3$.

8. A compound according to claim 7 wherein R is 2-chlorophenyl and R$^3$ is H.

9. A compound according to claim 1 wherein R$^1$ and R$^2$ are each alkyl.

10. A compound according to claim 9 wherein Y is —(CH$_2$)$_2$—.

11. A compound according to claim 10 wherein R$^3$ is hydrogen.

12. A compound according to claim 11 wherein R$^1$ is ethyl, R$^2$ is methyl and R is 2,3-dichlorophenyl.

13. A compound according to claim 11 wherein R$^1$ is methyl, R$^2$ is ethyl and R is 2-chloro-3-trifluoromethylphenyl.

14. A pharmaceutical composition comprising an anti-ischaemic or antihypertensive effective amount of a compound according to claim 1 and a pharmaceutically acceptable diluent or carrier.

15. A pharmaceutical composition comprising an anti-ischaemic or antihypertensive effective amount of a compound according to claim 7 and a pharmaceutically acceptable diluent or carrier.

16. A method of treating or preventing ischaemic heart disease in man which comprises administering an anti-ischaemic effective amount of a compound according to claim 1.

17. A method of treating or preventing hypertension in man which comprises administering an antihypertensive effective amount of a compound according to claim 1.

* * * * *

UNITED STATES PATENT AND TRADEMARK OFFICE

CERTIFICATE EXTENDING PATENT TERM
UNDER 35 U.S.C. § 156

PATENT NO.:      4,572,909

DATED:           February 25, 1986

INVENTOR(S):     Simon F. Campbell, et al.

PATENT OWNER:    Pfizer Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,252 DAYS with all rights pertaining thereto as provided by 35 U.S.C. § 156(b).

I have caused the seal of the Patent and Trademark Office to be affixed this 6th day of December 1993.

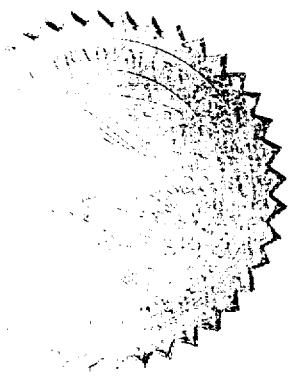

Bruce A. Lehman
Assistant Secretary of Commerce and
   Commissioner of Patents and Trademarks